(12) United States Patent
Andreucci et al.

(10) Patent No.: US 9,945,822 B2
(45) Date of Patent: Apr. 17, 2018

(54) MEASUREMENT SYSTEM INCLUDING A NETWORK OF NANOELECTROMECHANICAL SYSTEM RESONATORS

(71) Applicants: Commissariat A L'Energie Atomique Et Aux Energies Alternatives, Paris (FR); Apix Analytics, Grenoble (FR)

(72) Inventors: Philippe Andreucci, Moirans (FR); Régis Barattin, Grenoble (FR); Eric Colinet, Bois Guillaume (FR); Laurent Duraffourg, Voiron (FR); Pierre Puget, Saint Ismier (FR)

(73) Assignee: COMMISSARIAT A L'ENERGIE ATOMIQUE ET AUX ENERGIES ALTERNATIVES (FR)

( * ) Notice: Subject to any disclaimer, the term of this patent is extended or adjusted under 35 U.S.C. 154(b) by 235 days.

(21) Appl. No.: 14/432,665

(22) PCT Filed: Oct. 2, 2013

(86) PCT No.: PCT/EP2013/070594
§ 371 (c)(1),
(2) Date: Mar. 31, 2015

(87) PCT Pub. No.: WO2014/053575
PCT Pub. Date: Apr. 10, 2014

(65) Prior Publication Data
US 2015/0300999 A1    Oct. 22, 2015

(30) Foreign Application Priority Data
Oct. 2, 2012    (FR) .................................. 12 59339

(51) Int. Cl.
*G01N 30/64*    (2006.01)
*H03H 9/02*    (2006.01)
(Continued)

(52) U.S. Cl.
CPC ......... *G01N 30/64* (2013.01); *G01N 30/6095* (2013.01); *H03H 9/02259* (2013.01); *H03H 9/2457* (2013.01); *H03H 2009/02496* (2013.01)

(58) Field of Classification Search
CPC .............. G01N 30/64; G01N 30/6095; H03H 9/02259; H03H 9/2457;
(Continued)

(56) References Cited

U.S. PATENT DOCUMENTS

| | | | |
|---|---|---|---|
| 7,750,759 B1 | 7/2010 | Lee et al. | |
| 2005/0016276 A1* | 1/2005 | Guan | G01N 29/022 73/579 |

(Continued)

FOREIGN PATENT DOCUMENTS

| | | |
|---|---|---|
| EP | 2008965 A2 | 12/2008 |
| WO | 2011154362 A1 | 12/2011 |

(Continued)

OTHER PUBLICATIONS

"In-plane nanoelectromechanical resonators based on silicon nanowire piezoresistive detection" by Mile et al., Condensed Matter Physics 114-36, California Institute of Technology, Pasadena, CA 91125, USA.*

(Continued)

*Primary Examiner* — Paul West
*Assistant Examiner* — Xin Zhong

(57) ABSTRACT

The invention relates to a measurement system including a network of nanoelectromechanical system (NEMS) resonators, characterized in that: each one of said resonators includes: an electrostatic activation device capable of generating a vibration of a beam exposed to said excitation signal, at least one piezoresistive stress gauge made of a doped semiconducting material, extending from the beam so (Continued)

as to detect a movement of said beam, the variation in the electrical resistance of said at least one gauge supplying an output signal; said network includes at least two groups of resonators, each group including at least two resonators having an identical empty resonance frequency, each group of resonators having an empty resonance frequency different from that of each other group; the resonators forming each group are connected in parallel; the groups of resonators forming said network are connected in parallel; said system includes a reading device designed to supply an excitation signal at the network input and to determine the resonance frequency of a group of resonators which is selected by injecting, into said excitation signal, a frequency component corresponding to the empty resonance frequency of each selected group of resonators, and by identifying, in the output signal of the network, a resonance frequency component of the selected group of resonators.

17 Claims, 11 Drawing Sheets

(51) Int. Cl.
*H03H 9/24* (2006.01)
*G01N 30/60* (2006.01)

(58) Field of Classification Search
CPC ....... H03H 2009/02496; H03H 9/2447; H03H 9/2452; H03H 9/2463
See application file for complete search history.

(56) References Cited

U.S. PATENT DOCUMENTS

2009/0153258 A1 6/2009 Lutz et al.
2011/0003718 A1* 1/2011 Adams ................ G01N 29/022
506/39

FOREIGN PATENT DOCUMENTS

| WO | 2011154363 A2 | 12/2011 |
| WO | 2012034951 A1 | 3/2012 |
| WO | 2012034990 A1 | 3/2012 |
| WO | 2012172204 A1 | 12/2012 |

OTHER PUBLICATIONS

"Parallel array of noise-activated nonlinear micro-resonators with integrated actuators" by Yoshida et al., MEMS 2011, Cancun, Mexico, Jan. 23-27, 2011.*
Bargatin, I. et al., Large-Scale Integration of Nanoelectromechanical Systems for Gas Sensing Applications, Kavli Nanoscience Institute and Department of Physics, Caltech, American Chemical Society 2012.
Mile, E., et al., In-plane nanoelectromechanical resonators based on silicon nanowire piezoresistive detection, Condensed Matter Physics 114-35, California Institute of Technology, 2010.
Preliminary French Search Report for Application No. FR1259339 dated May 31, 2013.
International Search Report and Written Opinion for Application No. PCT/EP2013/070594 dated Nov. 18, 2013.

* cited by examiner

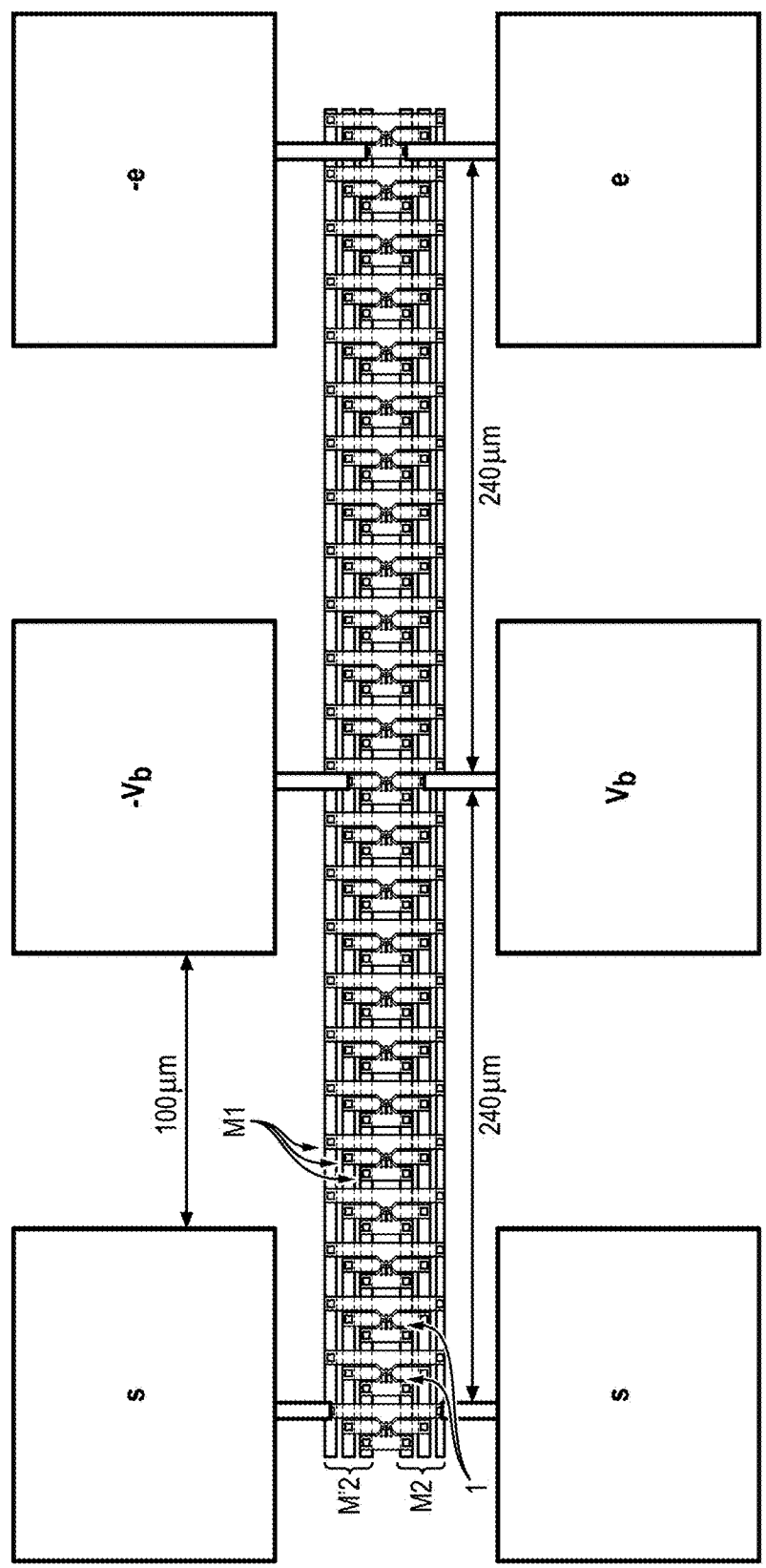

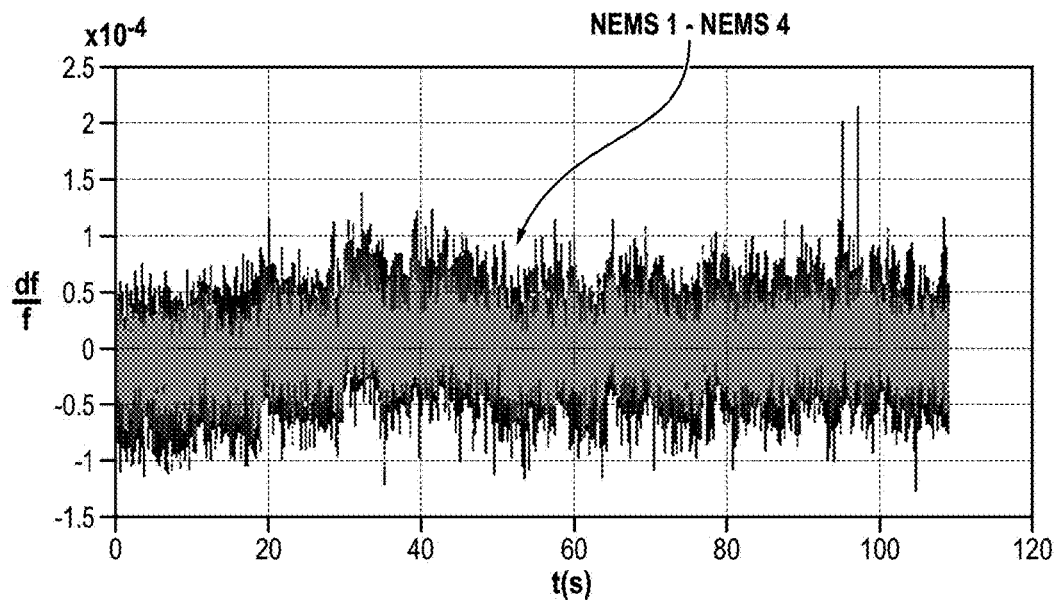
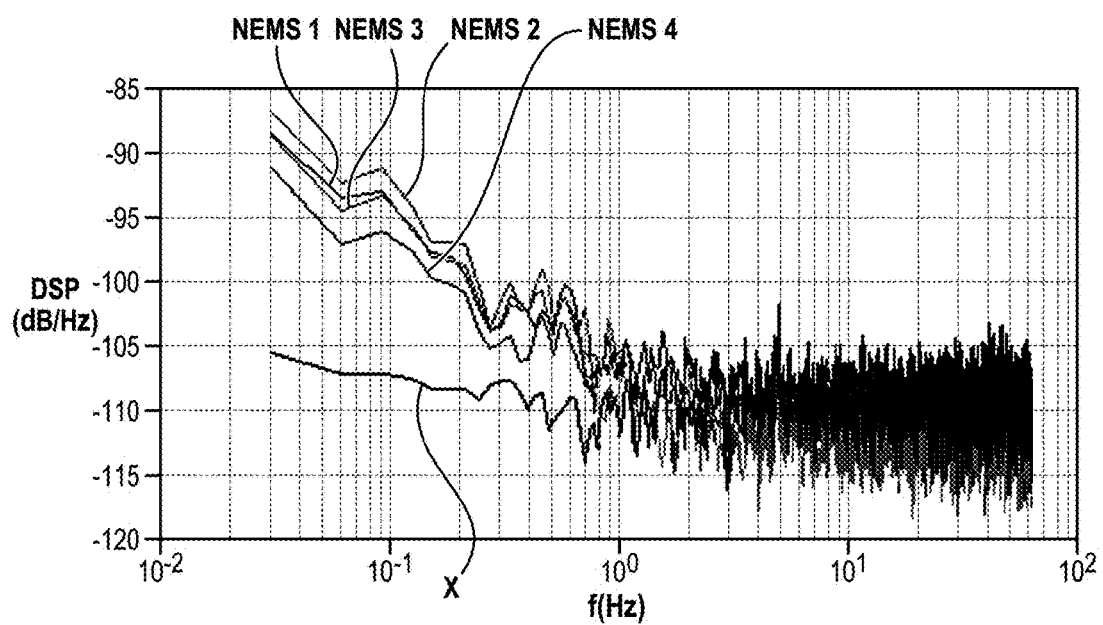

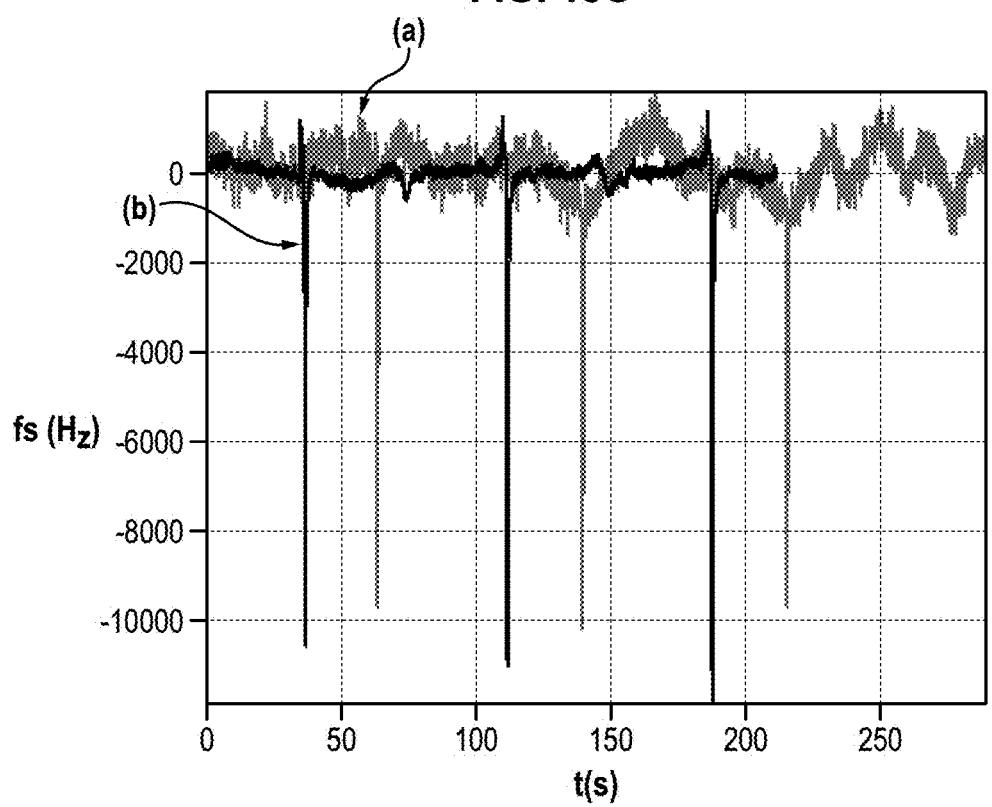

MEASUREMENT SYSTEM INCLUDING A NETWORK OF NANOELECTROMECHANICAL SYSTEM RESONATORS

CROSS REFERENCE TO RELATED APPLICATIONS

This application is a national phase entry under 35 U.S.C. § 371 of International Application No. PCT/EP2013/070594, filed Oct. 2, 2013, published in French, which claims priority from French Patent Application No. 1259339, filed Oct. 2, 2012, the disclosures of which are hereby incorporated herein by reference.

FIELD OF THE INVENTION

The present invention relates to a measurement system comprising a network of nanoelectromechanical system (NEMS) resonators.

BACKGROUND OF THE INVENTION

Nanoelectromechanical system (NEMS) resonators (generally denoted by the acronym NEMS for Nano Electro Mechanical System) are promising devices, particularly in the field of gas analysis.

The principle of detection of a species contained in a sample of said gas relies on the activation of a suspended beam of nanometer-scale dimensions at its resonant frequency, by way of an excitation signal (mechanical or electrical), and the detection of the displacement of said beam by means of at least one strain gauge.

The beam being functionalized by a given chemical substance, the passage of a sample of gas into a fluid channel wherein the resonator is placed enables the capture (for example by adsorption) by said substance of molecules of a species contained in the sample.

The capture of at least one molecule has the effect of modifying the resonant frequency of the beam, which is detectable in the output signal (generally electrical) of the strain gauge.

The resonator is connected to an electronic reading circuit, which firstly allows the beam to be activated into vibration by the excitation signal and secondly allows the output signal emitted by the strain gauge to be read.

Various structures of resonator have already been designed, comprising different types of beams (clamped-free, double-clamped etc.), different activation means (including thermoelastic, electrostatic activation means etc.) and a variety of detection techniques (including piezoresistive, piezoelectrical means etc.).

Such resonators can be fabricated on silicon substrates by means of the usual microelectronics techniques, including etching, deposition processes etc.

However, due to their nanometer-scale size, NEMS resonators are relatively fragile (particularly to mechanical and electrical impacts).

Moreover, their small surface area makes it difficult to capture species contained in very low concentrations in the samples to be analyzed.

To overcome these limitations, it can be advantageous to simultaneously use several resonators of this type, arranged in a network.

The expected advantages of a network of NEMS resonators are many.

Firstly, they offer a total surface area for capturing species for analysis which is larger if the number of beams is high.

This makes it possible to more accurately detect species contained in low concentrations in the gas sample to be analyzed.

Moreover, the use of a NEMS resonator network minimizes the impact of the failure of one of their number, which is compensated for by the operation of the other resonators of the network, thereby improving the robustness of the device.

Furthermore, for a network of N NEMS resonators, a detection limit gain in the order of $\sqrt{N}$ in terms of signal (or in the order of N in terms of power) could in theory be expected.

The detection limit can be estimated by calculating the Allan variance, which expresses the frequency measurement resolution (df/f ratio) as a function of the measurement time (also denoted by the term "integration time").

The obtaining of such a gain of $\sqrt{N}$ can be denoted by the term "network effect".

However, the production of a network of NEMS resonators comes up against various technological difficulties, in such a way that it has not been possible, to date, to fabricate a network allowing the expected network effect to be obtained.

Thus, the article by Bargatin et al. [Bargatin2012] describes a network of 2800 NEMS resonators connected in series and in parallel, wherein each resonator comprises a clamped-free silicon beam associated with a piezoresistive strain gauge composed of a metal layer deposited on the beam, the beam being thermoelastically activated in such a way as to vibrate out of the plane of the substrate in which it is fabricated.

The thermoelastic activation relies on the application to the resonators of an AC voltage at a frequency generating variations in the temperature of the beam at its resonant frequency.

To remove background noise, the authors employed differential measurement consisting in connecting two identical networks to the same input of the reading electronics, but applying a 180° phase shift to the signal sent to one of the networks with respect to the other, and by summing the output signals of each of the networks.

This article does however show disappointing results in terms of detection limit, particularly for long integration times, i.e. above 100 ms.

Thus, a detection limit comparable to that of an individual resonator was observed for integration times in the order of a few seconds.

According to the authors of the article, these results seem to be explained by problems of process variation in the resonance frequencies between resonators.

Specifically, the network effect cited above can only be obtained in ideal conditions, including in particular the hypothesis that the resonators of the network are perfectly identical to one another.

In practice, these conditions are difficult to achieve inasmuch as process variations, in particular, from one resonator to another are unavoidable.

[Bargatin 2012] thus indicates that the network used in the experiment exhibits variations in resonant frequency, which can be imputed to process variations, in the order of 1%.

As a result resonators with a response that is too different from that of the other resonators do not take part in the measurement, in such a way that, although the detection limit may be reduced, the network effect cannot be achieved.

The article by Mile et al. [Mile2010] presents an example of a different NEMS resonator from those used in [Bargatin2012].

This resonator comprises a clamped-free suspended beam, on either side of which extend two piezoresistive strain gauges made of doped silicon.

The activation of the beam is achieved electrostatically, by two electrodes set out on either side of the beam, leading to a vibration of the beam in the plane of the substrate in which is fabricated.

However, although this type of resonator, which has only been tested individually, appears promising in terms of signal-to-noise ratio, the measured Allan variance remains inexplicably higher than the theoretical variance due to an unknown form of noise, the nature of which has not been identified to date.

Now, the existence of this unidentified noise is likely to prevent the obtaining of a network effect if an attempt is made to combine said resonators in a network.

Indeed, if this noise is extrinsic to the resonators, or if it is intrinsic to the resonators but correlated from one resonator to another, a network effect cannot be obtained.

These phenomena must therefore be remedied to be able to produce a resonator network that effectively enables the desired network effect to be obtained.

Moreover, only collective addressing of the resonators is proposed in [Bargatin2012], i.e. all the resonators are connected to a single input and a single output, in such a way that it is not possible to read the output signal of each resonator.

In other words, the output signal of the network corresponds to the mean of the signals of the different resonators.

But it may be beneficial to address the resonators individually, i.e. to read the output signal of each resonator.

However, a NEMS resonator exhibits at least two, sometimes four interconnect pads for connecting with its reading electronics. Thus, for resonators of the type described in [Mile2010], when the activation mode and the detection mode are decoupled, i.e. different means are used, firstly for activating the beam and secondly for detecting its displacement, at least two pads are required for connecting the resonator to an activation circuit and at least two other pads are required for connecting to a detection circuit.

As a consequence, individual addressing of the resonators would suppose the multiplication of this number of interconnect pads by the number of resonators, which for a high number of resonators is technically impossible given the constraints relating to the overall size of the devices.

One aim of the invention is therefore to design a measurement system comprising NEMS resonators exhibiting improved performances in terms of detection limit and benefiting as much as possible from the expected network effect.

Another aim of the invention is to design a measurement system able to be fabricated according to a simple process that allows a system of small dimensions to be obtained.

BRIEF DESCRIPTION OF THE INVENTION

In accordance with the invention, a measurement system is proposed comprising a network of nanoelectromechanical system (NEMS) resonators, characterized in that:

each of said resonators comprises:
  an input for receiving an excitation signal and an output for supplying an output signal in response to said excitation signal, said output signal exhibiting resonance at the resonant frequency of the resonator,
  a beam suspended with respect to a support, the natural resonant frequency of the resonator corresponding to the natural resonant frequency of said beam,
  an electrostatic activation device capable of generating a vibration of said beam under the effect of said excitation signal,
  at least one piezoresistive strain gauge made of doped semiconductor material, suspended with respect to said support and extending from the beam in such a way as to detect a displacement of said beam, the variation in electrical resistance of said at least one gauge supplying said output signal, said network comprises at least two groups of resonators, each group comprising at least two resonators exhibiting an identical natural resonant frequency, each group of resonators exhibiting a different natural resonant frequency from that of each other group, the system comprises a memory wherein an item of information relating to the natural resonant frequency of each resonator or group of resonators is stored, the resonators forming each group are connected in parallel, each group comprising an input and an output respectively connected to the input and output of each of said resonators, the groups of resonators forming said network are connected in parallel, said network comprising an input and an output respectively connected to the input and the output of each of said groups of resonators, said system comprises a reading device designed to supply an excitation signal to the input of the network and to determine the resonant frequency of a selected group of resonators by injecting into said excitation signal a frequency component corresponding to the natural resonant frequency stored in the memory for each selected group of resonators and by identifying, in the output signal of the network, a frequency component at the resonant frequency of the selected group of resonators.

In the present text, the term "network" is understood to mean a dense arrangement of at least two groups of NEMS resonators connected in parallel.

The term "dense" refers to a density of at least 100 resonators/mm$^2$, preferably greater than or equal to 1000 resonators/mm$^2$.

In this way, all the resonators of the network are simultaneously subjected to the same environment and in particular to the same sample of gas to be analyzed.

In this respect, it should be noted that the document WO 2011/154363, wherein the arrangement of a plurality of NEMS resonators (denoted by the term "network") is described, does not concern a network in the sense of the present invention.

Indeed, unlike the present invention, in which care is taken to put all the resonators of a network into contact with the same sample to be analyzed, the aforementioned document aims to temporally and spatially distribute the gaseous sample to be analyzed by the plurality of resonators.

Said system can comprise a device for summing the output signals of each group of resonators of the network into a total output signal of the network, and the reading device is designed to determine the resonant frequency of a group of resonators from said total output signal of the network.

Advantageously, said reading device comprises a phase-locked loop (PLL) designed to lock a frequency of the excitation signal onto the frequency of a resonance peak of the output signal of the network and to supply the locked frequency as the excitation resonant frequency.

According to one embodiment, each group of resonators is functionalized with a different chemical species.

According to one form of network arrangement, the resonators of the network are arranged on one and the same support in such a way as to form rows and columns of resonators running parallel to one another, the beams of the resonators being parallel to one another.

According to another form of arrangement, the resonators of the network are arranged on one and the same support in such a way as to form rows and columns of resonators running parallel to one another, said resonators being further arranged in such a way that, on one and the same row parallel to the beams of the resonators, two adjacent resonators are symmetrical with respect to a plane parallel to a column.

Preferably, the system comprises at least one fluid channel intended for the flow of a gas sample to be analyzed, said network of resonators being arranged in said fluid channel in such a way that the beams of said resonators are exposed to said sample.

The system can furthermore comprise at least two networks of resonators in said fluid channel.

According to an advantageous form of execution, the system comprises at least one said reference resonator arranged outside the fluid channel while being subjected to the same external fluctuations, and connected to the same reading device as the network arranged in the fluid channel; the system furthermore comprises a processing system configured to combine the output signal of said reference resonator with the output signals of the groups of resonators of the network.

According to another advantageous form of execution, the system comprises at least one said reference resonator configured to be less sensitive to the gas sample than the other groups of resonators; the system furthermore comprises a processing system configured to combine the output signal of said reference resonator with the output signals of the groups of resonators of the network.

The system can also comprise a processing system configured to combine the output signals of each group of resonators of the network with a mean of said signals.

Moreover, the system can comprise a gas chromatography column containing said fluid channel.

Advantageously, the channel of said chromatography column comprises a plurality of resonator networks distributed regularly between the input and the output of said column.

Alternatively, the system can comprise a gas chromatography column upstream of said fluid channel in the direction of flow of the gas sample.

Another aspect of the invention relates to a method for reading a system as described above, characterized in that it comprises the steps consisting in:

selecting a group of resonators to be read, from among the groups of resonators of the network, retrieving from the memory the natural resonance information of each selected group of resonators, applying an excitation signal to the network comprising a frequency component corresponding to the natural resonant frequency of each selected group of resonators, determining the resonant frequency of each selected group of resonators by identifying, in the output signal of the network, a resonant frequency component of each selected group of resonators.

Thus, preferably, the application of said excitation signal generates in the output signal a core frequency component corresponding to the resonance of each selected group of resonators, and the resonant frequency of each selected group of resonators is determined by extracting said frequency component from the output signal of the network.

Another aspect of the invention concerns a process of fabrication of a system as described above, characterized in that it comprises the collective fabrication, on a support made of a semiconductor material, of the resonators forming said network by employing microelectronics techniques.

Advantageously, said process comprises the collective functionalization of the groups of resonators of said network by chemical vapour deposition (CVD) or physical vapour deposition (PVD) of different chemical species for each of said groups.

BRIEF DESCRIPTION OF THE DRAWINGS

Other features and advantages of the invention will become apparent on reading the following detailed description, with reference to the appended drawings wherein:

FIG. 4 is a top view diagram of the connection of the various resonators of the network;

FIG. 7 shows the Allan variance measured for a network of 4 resonators;

FIG. 8 shows the power spectral density of the signals of each of the resonators and of a signal reconstructed by fusion of said signals;

FIG. 13C showing the superimposition of these two signals.

DETAILED DESCRIPTION OF EMBODIMENTS OF THE INVENTION

There follows a sequential description of the various elements of the system, after which the operation of said system will be described.

Description of an Embodiment of a Resonator

Figure 1:
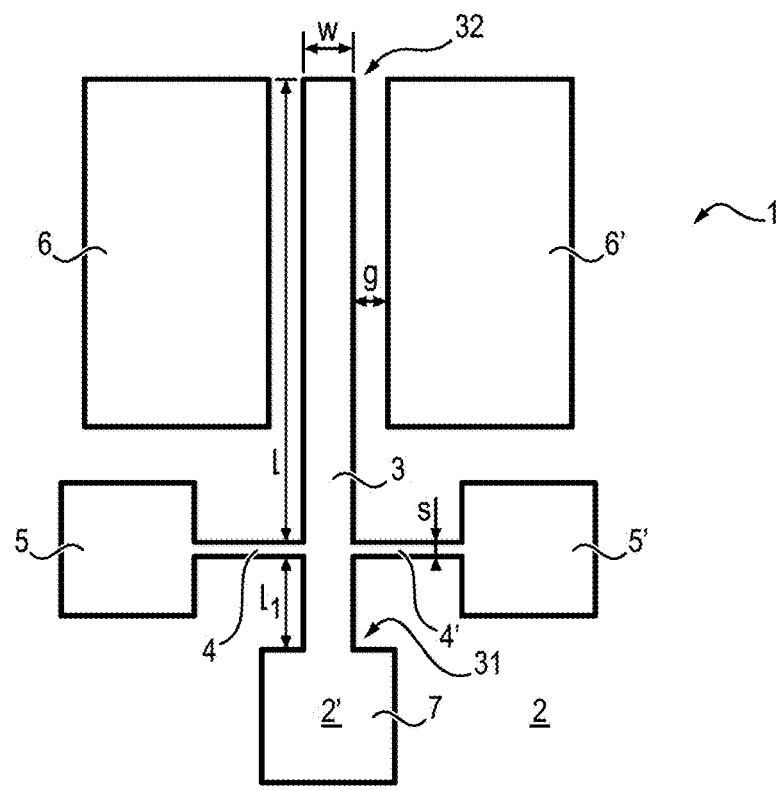
FIG. 1 is a top view diagram of an embodiment of a NEMS resonator forming part of a system according to the invention.

FIG. 1 shows a top view of a resonator according to an embodiment of the invention.

Said resonator 1 is formed on a support substrate 2.

The resonator comprises a beam 3 of length L and of width w.

The beam 3 is suspended with respect to the support substrate 2, with the exception of the clamping of one of its ends 31 in a part 2' of the substrate, projecting with respect to the plane of the substrate 2 which extends under the beam 3.

In a manner known per se, such a beam can be formed by etching the substrate 2.

The other end 32 of the beam is free.

On either side of the beam 3 extend two piezoresistive strain gauges 4, 4', which are also suspended with respect to the substrate 2.

Advantageously, said gauges 4, 4' are, like the beam, etched into the substrate 2 and have at least one plane in common with the beam 3.

These gauges are made of doped semiconductor material, preferably having a dopant concentration above $10^{19}$ atoms/$cm^3$, and have a cross-section s.

According to an embodiment given for information purposes, the width of a gauge is of 100 nm, its thickness of 160 nm and its length of 500 nm.

Preferably, said doped semiconductor material is doped silicon.

The intersection between each of the gauges 4, 4' and the beam 3 is found at a distance $l_1$ from the region 31 where the beam is clamped, chosen to maximize the strain exerted on the gauge during the deflection of the beam.

Each of the gauges 4, 4' is linked to an electrode 5, 5', said electrodes allowing the respective application of constant potentials of opposite signs.

In other embodiments of the resonator, it is possible to use only one strain gauge made of doped semiconductor material.

The resonator 1 furthermore comprises a device for electrostatic activation of the beam which, as represented here, can comprise two electrodes 6, 6' extending in the same plane as the beam and which are arranged on either side of the latter, at a distance g.

The electrodes 6, 6' are respectively intended to receive an electrical excitation signal and a signal of opposite sign, and therefore constitute two inputs of the resonator.

Under the application of an electrical signal having a frequency corresponding to the natural resonant frequency of the beam 3, the beam is led to vibrate in a plane parallel to the substrate 2.

The term "natural resonant frequency of the beam" is understood to mean the resonant frequency of the beam in the absence of the gas to be analyzed.

According to one embodiment, the measurement of the variation in the electrical resistance of the piezoresistive gauges is taken between the clamped end 31 of the beam and the junction between the beam and the gauges 4, 4'.

The output signal of the resonator is thus supplied to a connection electrode 7 situated at the clamped end 31 of the beam with a view to reading said signal.

This measurement method is however not exclusive and the output signal can be supplied by other means; for example, it is possible to apply a bias voltage at the electrode 7 and to measure the voltage across the terminals of the assembly of the two gauges 4, 4' to deduce the variation in their electrical resistance therefrom.

Those skilled in the art will therefore be able to adjust the design of the biasing of the strain gauge(s) and of the measurement of their response without departing from the scope of the present invention.

For purely informative purposes, the dimensions of the beam of such a resonator are in the order of a few micrometers in length, of a few hundred nanometers in width, and of a hundred nanometers in thickness.

Thus, according to an embodiment given by way of example, the beam has a length of 3 to 4 µm, a width of 300 nm and a thickness of 160 nm.

The reader is also referred to the documents [Mile2010] and EP 2 008 965, which describe such a resonator.

However, this way of producing the resonator is not limiting and in documents WO 2012/034990 and WO 2012/034951 the reader may find other examples of resonators able to be implemented in a system according to the invention, with in particular different modes of beam clamping.

All these embodiments of resonators have at least the following features in common:
- an input for receiving an excitation signal and an output for supplying an output signal in response to said excitation signal, said output signal exhibiting resonance at the resonant frequency of the resonator,
- a beam suspended with respect to a support, the natural resonant frequency of the resonator being defined as being the natural resonant frequency of said beam,
- an electrostatic activation device capable of generating a vibration in said beam under the effect of said excitation signal,
- at least one piezoresistive strain gauge made of doped semiconductor material, suspended with respect to said support and extending from the beam in such a way as to detect a displacement of said beam, the variation in electrical resistance of said at least one gauge supplying said output signal.

Such resonators offer the following advantages specifically.

Firstly, the use of an electrostatic force makes it possible to substantially reduce the power necessary to activate a resonator (which is in the order of 1 microwatt or less), which reduces the constraints on the interface electronics.

By comparison, the power required to activate a resonator thermoelastically, as in [Bargatin2012], can be estimated at 1 milliwatt.

Regarding this, the inventors have identified as one of the possible causes of the disappointing performance of the network described in this document the need for interface electronics that are very complex and liable to be incapable of delivering the power required for all the resonators of the network.

Due to this fact, these resonators seem not to have been sufficiently activated for their output electrical signal to be clearly above the noise of the reading electronics.

As a consequence, the predominant noise source therefore seems to be the pink noise of the reading electronics, which is external to the network of resonators.

Figure 2:
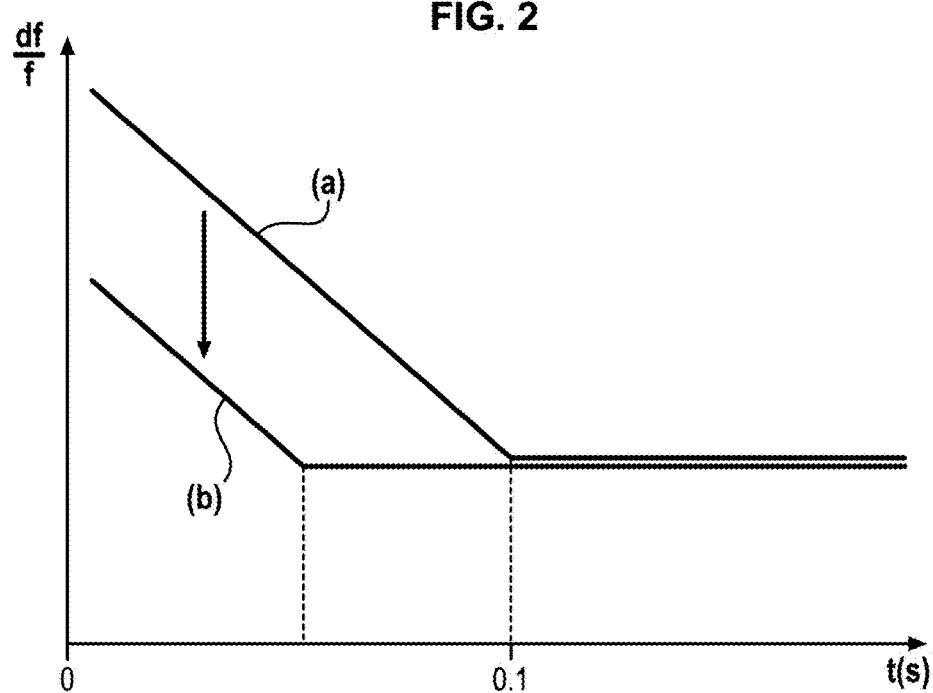
FIG. 2 is a schematic representation of the Allan variance for an individual resonator and for a network of resonators of the prior art.

FIG. 2 schematically illustrates the Allan variance for an individual NEMS resonator (curve (a)) and for a network of NEMS resonators as described in [Bargatin2012] (curve (b)).

On this graph, the abscissa represents the integration time t and the ordinate represents the frequency measurement resolution, defined by the df/f ratio.

The time period of 100 ms corresponds to a limit between white noise (for which an increase in integration time improves resolution) and pink noise (also called 1/f noise)

(for which an increase in integration time has no effect on resolution) for an individual resonator.

Comparing curves (a) and (b) shows that networking NEMS resonators has an effect on the white noise of the resonators, which is uncorrelated from one resonator to another, since it makes it possible to improve the measurement resolution for low integration times.

On the other hand, no network effect is observed for high integration times which correspond to pink noise, which is generated, as cited above, by the reading electronics.

Another advantage of the resonators employed in the invention is that they can be fabricated on a semiconductor substrate, silicon for example, by employing techniques well known in the field of microelectronics, mainly consisting of photolithography and etching.

It is thus possible to dispense with the metallization process (of "sputtering" type) which is employed in the fabrication of the metallic gauges in [Bargatin2012], which is responsible for process variation.

It is thus possible to obtain less process variation, which is a factor of obtaining the expected network effect.

Moreover, the decoupling of the activation and the detection makes it possible to significantly reduce the background signal, unlike the metallic resonators described in [Bargatin 2012], wherein the same resistor is used to activate and detect.

Indeed, in these metallic resonators, the variation in electrical resistance of the metal gauge results firstly from the deformation of the gauge (i.e. the desired information) and its self-heating (which constitutes a parasitic signal).

Thus, with the resonators used in the invention, the measurement is not subject to fluctuations related to the activation of the beam.

Spatial Arrangement of the Resonators of the Network

One peculiarity of a network implemented in a system according to the invention is the density of the resonators belonging to said network.

More precisely, a density above 100 resonators/mm$^2$, preferably above 1000 resonators/mm$^2$ is appropriate for such a network.

Specifically, this density makes it possible to ensure that all the resonators of the network are simultaneously subjected to the same environment, and particularly to the same sample of gas to be analyzed.

In addition, it makes it possible to reduce the risks of process variations between resonators, these variations being greater when the network is extended in space.

Moreover, this density makes it possible to form a network formed of a large number of resonators which is compact enough to be able to be introduced into a fluid channel in which the gas sample to be analyzed circulates, transported by a carrier gas.

Regarding this, it should be noted that that the network described by [Bargatin2012] occupies a surface area of 0.14 mm by 1 mm, which is poorly compatible with incorporation into a fluid channel, the cross-section of which is typically equivalent to that of a channel with a circular cross-section of a diameter less than or equal to 1 mm (such a channel is generally denoted by the term "microfluidic").

Finally, a high density of resonators makes it possible to cover the surface area of the fluid channel as well as possible, and consequently makes it possible to provide more accurate information on the composition of the sample to be analyzed.

Figure 3A:
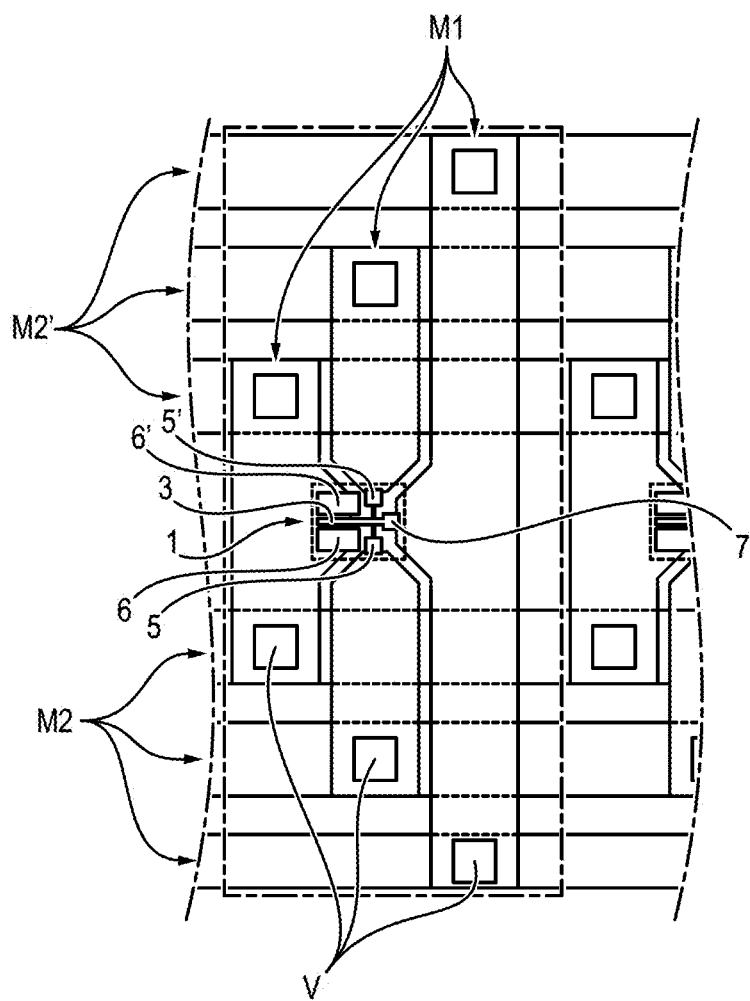
FIG. 3A is a top view diagram of a first example of a dense arrangement of networked NEMS resonators.
Figure 3B:
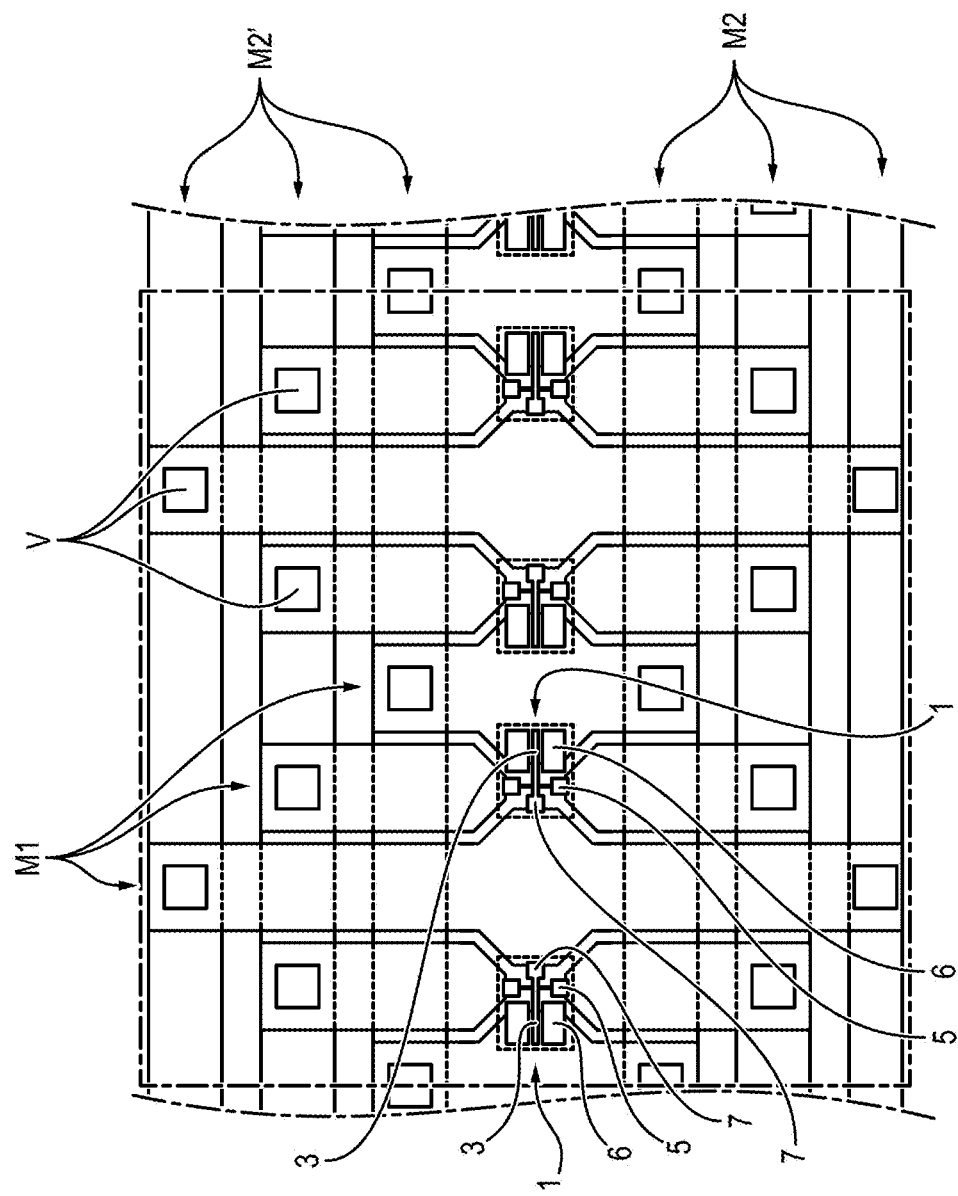
FIG. 3B is a top view diagram of a second example of a dense arrangement of networked NEMS resonators, providing a greater density than that of the example in FIG. 3A.

FIGS. 3A and 3B illustrate two modes of arrangement of the NEMS resonators allowing the desired density to be obtained.

FIG. 3A illustrates a top view of part of a network of resonators of the type illustrated in FIG. 1 according to a first embodiment.

In this figure, only one resonator 1 is represented.

The box in bold dotted lines denotes a mesh of the network, the network being composed of a plurality of such adjacent meshes arranged in rows and/or columns.

The two levels of interconnecting rows allowing the electrical connection of the resonators are also represented.

A first level of parallel metal interconnection rows is denoted by the reference M1 (vertical lines on FIG. 3A).

In this level, a first pair of rows (the leftmost on the elementary mesh in FIG. 3A) are connected to the electrostatic activation electrodes 6, 6'; a second pair of rows (at the center of the elementary cell) are connected to the electrodes 5, 5' for applying potential to the strain gauges; finally, a third interconnection row (the rightmost on the elementary cell in FIG. 3A) is connected to the output electrode 7 of the resonator.

A second level of metallic interconnection rows is denoted by the references M2 and M2' (horizontal lines in FIG. 3A).

The rows M2, M2' are mutually parallel and perpendicular to the interconnection rows of the first level.

The rows M2 and M'2 respectively are three in number and run symmetrically with respect to the longitudinal axis of the resonator.

Two rows (those closest to the resonator) are intended for transmitting the excitation signal of the resonators; two rows (those furthest from the resonator) are intended for transmitting the output signal of the resonators; finally, two rows (intermediate between the aforementioned two pairs of rows) are intended for applying the bias voltage of the electrodes of the strain gauges.

For this purpose, the rows M2, M'2 are connected by interconnect vias V to the corresponding rows of the first interconnection row M1.

Purely for information purposes, this configuration can be obtained with an elementary mesh size having a length (parallel to the beam) of 18 μm and a width of 41.2 μm, or else of 10.5 μm by 26.3 μm, or else of 7.5 μm by 20.3 μm.

Naturally, the organization of these interconnection levels can be modified by those skilled in the art without departing from the scope of the invention.

To form the network, each resonator is connected in parallel to the second level of interconnection rows M2, M'2, by means of a first level of interconnection rows of the same type as the rows M1 described above.

FIG. 3B illustrates in top view a part of a network of resonators of the type illustrated in FIG. 1 according to another embodiment.

Compared to the network in FIG. 3A, the network in FIG. 3B is even denser.

The two interconnection levels described with reference to FIG. 3A are similar and will therefore not be described again.

In this network, the resonators are arranged "head to tail", i.e. in a row of resonators arranged in parallel, each resonator has two neighbors that are each symmetrical to it with respect to a plane perpendicular to the longitudinal axis of the beams.

This makes it possible for two resonators to have the rows of the first interconnection level intended to transmit the excitation signal as well as the row for transmitting the output signal in common, hence a gain in the compactness of the system.

Purely for information purposes, with this configuration it is possible to obtain a dimension of elementary mesh (comprising 4 resonators) having a length (parallel to the beam) of 44 μm and a width of 41.2 μm, or else of 28 μm by 26.3 μm, or even of 20 μm by 20.3 μm.

Based on this principle, it is therefore possible to organize, for example, matrices composed of several rows and columns of resonators arranged in the pattern in FIG. 3A or that in FIG. 3B.

FIG. 4 illustrates in top view the electrical connection of a network of resonators according to the arrangement illustrated in FIG. 3A.

The rows M2, M2' of the second interconnection level of the resonators are connected to two output electrodes for transmitting the output signal s, two electrodes for applying the bias voltages Vb, −Vb to the strain gauges and two input electrodes for applying the excitation signal e, −e.

Organization of the Network into Groups of Resonators

Moreover, and unlike the network described in [Bargatin 2012], not all the resonators of the network have the same natural resonant frequency.

Indeed, the network comprises at least two groups of at least two resonators, the resonators of each group having an identical natural resonant frequency, different from the natural resonant frequency of the resonators of each of the other groups.

In the remainder of the text, the term "natural resonant frequency" of a group denotes the natural resonant frequency of each of the resonators forming said group, it being understood that within one and the same group all the resonators have an identical natural resonant frequency.

The term "different" is understood to mean that, in a series of increasing natural resonant frequencies, a natural resonant frequency is greater by at least 1% than the natural resonant frequency immediately below it.

The term "group" is understood not only in terms of identical features of the resonators (same natural resonant frequency) but also spatially, the resonators of one and the same group being adjacent and consequently gathered together over a small portion of the total surface area of the network.

The distance between groups of resonators can be identical to the distance between two resonators of one and the same group.

Alternatively, two adjacent groups can be separated by a distance greater than the distance separating two resonators; for example, according to fabrication constraints, a certain distance may be inserted between adjacent groups that one wishes to functionalize differently.

Generally, the dimensions of the network are limited by the diffusion length of the gas sample, which is in the order of the millimeter.

The number of resonators can be identical for all the groups or vary from one group to another.

The electrical connection of the resonators of the network is effected in the following way.

Firstly, the resonators forming one and the same group are connected in parallel, each group comprising an input and an output respectively connected to the input and the output of each of said resonators, Secondly, the groups of resonators forming the network are connected in parallel, said network comprising an input and an output respectively connected to the input and the output of each of said groups of resonators.

Thus, the number of inputs and outputs of the network is identical to that of a single resonator, which does not complicate the electrical architecture.

This breaking down of the network into groups of resonators has the following advantages.

Firstly, it makes it possible to limit the effects of process variation.

Indeed, the process variation from one resonator to another is larger if the resonators are further from one another.

Thus, even if the network is very compact thanks to an optimal arrangement of the resonators, two resonators situated at two opposite ends of the network are liable to exhibit non-negligible process variation.

On the other hand, within one and the same group, variation between resonators is minimized.

Moreover, even if variation exists between separate groups of resonators, it is possible to avoid it by way of a mathematical correction, each group being addressed independently of the others.

Another advantage of this breaking down of the network into groups is the possibility of functionalizing the resonators belonging to different groups with different chemical species.

Thus, if the chemical species used for functionalization are carefully chosen as a function of the gas sample to be analyzed, one and the same network is able to simultaneously supply information on several species contained in the sample.

Advantageously, the obtaining of different natural resonant frequencies between groups of resonators is due to the production of resonators with beams that are of different lengths from one group to another, their mechanical and geometrical features being moreover identical.

Specifically, the natural resonant frequency F* of a resonator is defined by the following formula:

$$F^* = \frac{1}{2\pi}\sqrt{\frac{EI}{\rho s}\left(\frac{2.1178}{L}\right)^2}$$

with $$I = \frac{w^3 e}{12}$$

and s=w e, where E is the Young's modulus of the material forming the NEMS resonator, ρ its density, I the moment of inertia of the resonator, s its cross-section, L and w the length and width respectively of the vibrating beam, and e its thickness.

The dimensioning of the resonators of each group is carried out by determining, for each group of resonators, an interval of maximum expected variation of the resonant frequency and by choosing beam lengths (or another mechanical feature of the resonator) defining natural resonant frequencies sufficiently spaced apart from one another that the abovementioned variation intervals do not overlap.

Preferably, safety margins are taken into consideration to take account of any process variations.

Using such dimensioning of the resonators in each of the groups, it is possible to obtain the information about the groups of resonators in the network separately and with high accuracy.

Figure 5:
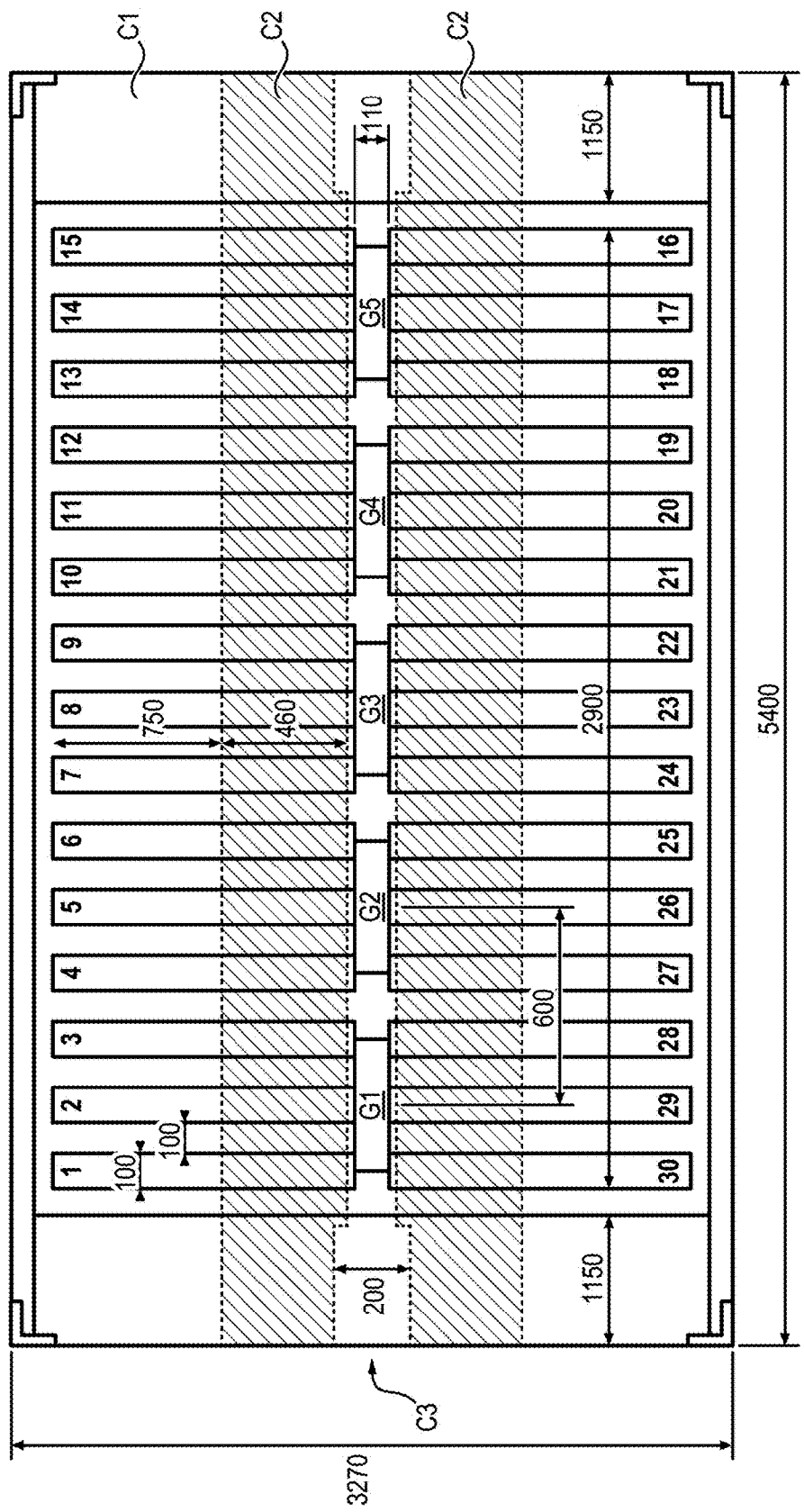
FIG. 5 schematically illustrates in top view the arrangement of a network composed of 5 groups of resonators in a fluid channel.

FIG. 5 illustrates in top view an example of an implementation of a network as described above in a fluid channel.

Said channel is etched into a support, for example made of silicon, and bonded to the support of the NEMS resonators, which is here a doped silicon chip, with the reference C1.

The hatched surfaces C2 correspond to the bonding interface of the support that is applied to the chip C1 in order to form a fluid channel on the chip C1.

The fluid channel thus inserted is referred to by the reference C3.

The dimensions appearing in this figure are expressed in micrometers and are provided with the simple aim of supplying a particular example of an implementation of a measurement system, without in any way limiting the invention.

In this example, the network comprises 5 groups of resonators G1 to G5, each group having a different natural resonant frequency.

The vertical strips numbered 1 to 30 denote the tracks connecting to the input, the output and the strain gauge bias of each of the resonator groups.

In the context of a gas analysis system, the fluid channel in which the network is arranged can typically be arranged downstream of a chromatography column.

The fluid connecting means between the column and such a channel are known per se: they can be a capillary of deactivated silica or, if the chromatography column is itself etched into a silicon chip, as described in document WO 2011/154362, the fluid channel can optionally be etched into the same chip.

Alternatively, at least one network as described above can be arranged on the inside of a chromatography column etched into a silicon chip.

Particularly advantageously, it is possible to instrument said column by installing therein a plurality of networks regularly distributed between the input and the output of said column.

Reading of the Network

The reading of the network relies on the individual addressing of the various groups of resonators, the resonators of one and the same group being addressed collectively.

Since this addressing is carried out on the basis of the resonant frequencies of each group of resonators, it can be described as frequency addressing.

Figure 6:
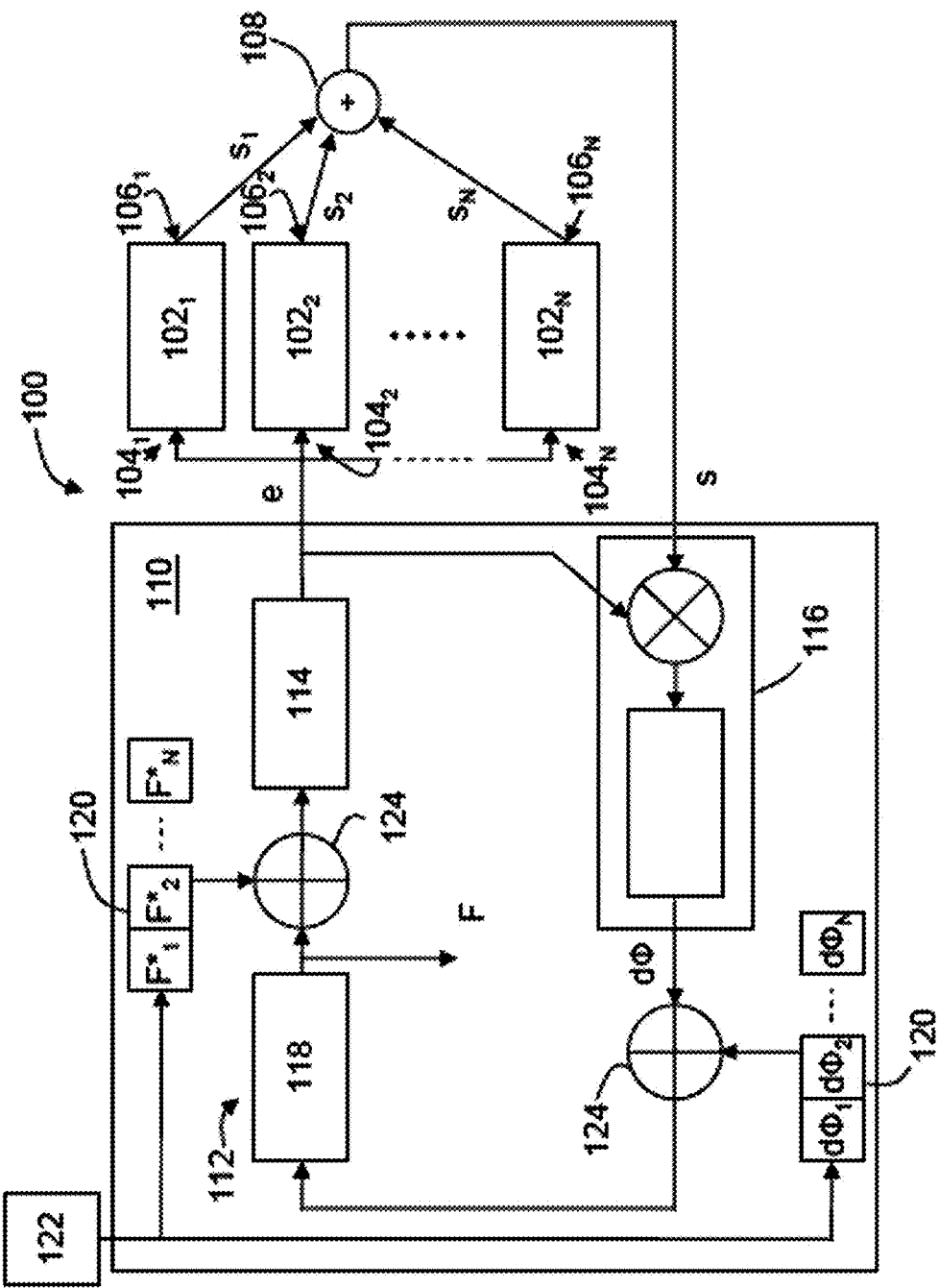
FIG. 6 is a diagram of the electronic reading architecture of such a network.

FIG. 6 schematically illustrates the electrical architecture of the system,

Each group of NEMS resonators of the network is denoted by the reference $102_i$, where I is an integer between 1 and N, N being the number of groups forming the network.

Each of these groups is provided with an input $104_i$ for receiving an excitation signal and an output $106_i$ for supplying an output signal.

When an excitation signal e, comprising a frequency component corresponding to the natural resonant frequency (denoted $F^*_i$) of the resonators of the group, is applied to the input 104i of each group of resonators, the beams of the resonators are set to vibrate, which translates into the generation, by the strain gauges associated with each beam, of an electrical output signal that corresponds to the excitation signal e, considerably amplified around the resonant frequency $F_i$.

Since the resonators of one and the same group are arranged in parallel and addressed collectively, the output signal $s_i$ of the group is a combination of the signals of each resonator.

The system furthermore comprises a device 108 for summing the output signals $s_i$ into a total output signal s.

The system moreover comprises a device 110 for reading the groups of resonators $102_i$, which is designed to supply the excitation signal e to the input of the network, said excitation signal being supplied to each group of resonators.

The reading device 110 is furthermore designed to determine the resonant frequency of a selected group of resonators by injecting into said excitation signal e a frequency component corresponding to the natural resonant frequency stored in the memory for each selected group of resonators and by identifying, in the total output signal of the network, a frequency component of a selected group of resonators.

In a preferred embodiment, the reading device comprises a phase-locked loop 112 (PLL).

Said circuit 112 is advantageously designed to lock a frequency of the excitation signal onto the frequency of a resonance peak of the output signal of the network and to supply the locked frequency as the excitation resonant frequency.

For this purpose, the phase-locked loop 112 comprises a voltage controlled oscillator 114 which is controlled by a voltage F and connected to the inputs 104i of the groups of resonators 102i to supply the excitation signal e to them, said signal being periodic and single-frequency, of a frequency corresponding to the voltage frequency F.

The circuit 112 furthermore includes a phase comparator 116 connected to the summing device 108 for receiving the total output signal s and designed to determine and supply a phase shift dφ between the total output signal s and the excitation signal e.

The circuit 112 furthermore includes a controller 118 compared to the phase comparator 114 and designed to determine and supply the voltage F to the voltage controlled oscillator 114 based on the phase shift dφ.

The reading device 110 furthermore comprises a memory 120 wherein are stored, firstly, the natural resonant frequencies $F^*i$ of the groups of resonators, and secondly, an initial phase shift dφi for each group 102i of resonators.

Moreover, the reading device 110 comprises means for selecting each of the stored natural resonant frequencies $F^*i$ and each of the initial phase shifts dφi stored in said memory 120.

One advantage of using a phase-locked loop (PLL) compared to another device, such as an oscillator or an open loop as proposed in the abovementioned articles, is to better avoid variations.

Indeed, although the phase-locked loop is more bulky and more complicated than an oscillator which only requires a few transistors and employs a simple analog-to-digital conversion (counters), the phase-locked loop is more robust to noise and process variation. It furthermore makes it possible to select the mode of resonance and has an adjustable passband or response time.

Differential Measurement

A network as described above has the advantage of exhibiting very low noise.

In some situations, it may be advantageous to remove noise extrinsic to the network by employing differential measurement relying on a reference resonator or network of resonators, making sure that the reference resonator or network of resonators is subjected to the same environment liable to generate fluctuations, but that this resonator or network of resonators has a response to the gas sample that is different from that of the network under consideration.

Indeed, differential measurement eliminates the influence of external parameters, other than the adsorption of the gas by the NEMS resonators—which are responsible for a modification in the resonant frequency of the NEMS. By way of example, these include variations in temperature, variations in the flow of the carrier gas, etc.

The principle of this method is explained hereinbelow based on a target NEMS resonator from which one is seeking to remove extrinsic noise, and a reference NEMS resonator making it possible to employ differential measurement, but it goes without saying that it is also applicable if the target resonator and/or the reference resonator are replaced with a network comprising one or more groups of collectively addressed resonators.

The effectiveness of this measurement method relies essentially on the fact that the two NEMS resonators are situated as close as possible to one another, in such a way as to be subjected to the same fluctuations, and that one of the NEMS resonators is not sensitive (or is very poorly sensitive) to the gas to be identified.

Two embodiments make it possible to meet these conditions.

According to a first embodiment, the NEMS are installed in two separate fluid channels.

Thus, one of the NEMS will be subjected to the carrier gas and to the sample of gas to be analyzed, whereas the other (reference resonator) will be subjected to the carrier gas only.

According to a second embodiment, two NEMS resonators functionalized differently are placed in the same fluid channel.

By choosing two very different functionalizations in terms of adsorption of the gas to be analyzed, it is then possible to take a differential measurement. For this purpose, one of the NEMS is functionalized with a chemical species sensitive to the sample of gas to be analyzed whereas the other NEMS is not functionalized by deposition of a specific layer (said resonator can, for example, be naturally oxidized), or is functionalized for a chemical species not sensitive to the gas to be analyzed. For example, the target NEMS resonator can be functionalized with SiOC and the reference resonator is simply covered with a layer of native oxide.

Whatever the chosen measurement architecture, the electrical measurement of the two NEMS resonators must be carried out individually in order to dissociate the fluctuation in the resonant frequency of the one from the other.

Several electrical reading approaches are possible:
- a measurement carried out via 2 separate sets of electronics (parallel reading). However, this first approach is not favored because it does not remove fluctuations associated with the reading electronics;
- a measurement carried out via the same set of electronics by carrying out a time-sequential measurement (each NEMS resonator is read alternately over a period in the order of 1 ms in order to ensure a quasi-simultaneous reading of the two NEMS: the concept of quasi-simultaneity is defined with respect to the duration of a gas peak and the fluctuations in the resonant frequency of the NEMS; in practice, the reading time of each NEMS resonator is less than or equal to 100 ms).

This second approach removes the fluctuations in the reading electronics in addition to the environmental fluctuations, which can affect the resonant frequency of the NEMS resonators.

The practical implementation of this measurement can be carried out using frequency addressing (two NEMS resonators with two natural resonant frequencies connected in parallel) or else with the use of a switch to switch from one NEMS resonator to the other over time.

Once the simultaneous measurement (or quasi-simultaneous measurement on the scale of the duration of the gas peaks) of the two NEMS resonators has been carried out, the signal processing work mainly consists in subtracting the response of the reference NEMS resonator from the response of the target NEMS resonator to thus eliminate all the fluctuations in the resonant frequency induced by external parameters other than the gas sample being adsorbed onto the NEMS resonators.

In the context of the measurement system according to the invention, the reference resonator or group of resonators can be part of the network itself, and not include any specific functionalization so as to be notably less sensitive than the other groups of resonators to the gas sample to be analyzed.

As mentioned above, this differential measurement principle is not limited to a NEMS network but can be implemented in a general way to remove fluctuations external to a NEMS resonator, whether or not it is part of a network.

The comparison of the signals of said resonator and a reference resonator makes it possible to improve the signal-to-noise ratio of said resonator.

Operation of the System

During a calibration operation, the natural resonant frequencies $F^*i$ and the initial phase shifts $d\phi i$ are determined by for example scanning the frequency space in open loop with the voltage-controlled oscillator 114.

This data is stored in the memory 120.

In operation, the gas sample to be analyzed, which is carried by a carrier gas, is made to flow through the fluid channel in which the network of resonators is arranged.

In general, the carrier gas and the sample come from a chromatography column arranged upstream.

During an operation of reading a group of resonators 102*i*, the selection means 122 select the natural resonant frequency $F^*i$ and the phase shift $d\phi i$ of said group of resonators that one wishes to read.

The starting means then inject these values into the phase-locked loop 112, in such a way as to ensure that said loop 112 locks onto the resonant frequency of the group of resonators 102*i*.

Thus, at the end of a lock time which is generally in the order of 50 µs, the locked frequency F corresponds to the resonant frequency of the group of resonators 102*i*.

The reading operation is repeated in sequence for all the groups of resonators forming the system.

Subsequently, the physical quantity whose measurement is sought by the measurement of the group of resonators (for example, the mass of a species of the gas sample adsorbed onto the beams of the resonators of said group) is determined from the read resonant frequency and from the natural resonant frequency of said group of resonators, for example based on the difference between the resonant frequency and the natural resonant frequency.

This determination is within the reach of those skilled in the art specializing in gravimetric analysis of gases and will therefore not be detailed here.

It should also be noted that other modes of embodiment of the reading device may be implemented without departing from the scope of the invention. In this regard the reader is referred to the application PCT/FR2012/050682 filed Mar. 29, 2012.

Signal Processing

Once the output signals of each group of resonators (denoted $x_i(t)$) have been read, they are fused so as to obtain a signal $X(t)$ exhibiting improved features.

For this purpose, the measurement system includes a processing system implementing a fusion algorithm.

Various algorithms enable such a fusion of data to be carried out and are within the reach of those skilled in the art, according to the features of the individual signals.

Generally, data fusion consists in combining signals, preferably in comparing them, for example by subtraction or division.

For example, in the case where the forms of noise of each group are totally independent (uncorrelated) from one another, fusion can consist in taking a spatial mean of said signals after normalizing them, according to the formula:

$$X(t) = \frac{1}{N}\sum_{i=1}^{N} \frac{xi(t) - <xi(t)>}{<xi(t)>} \quad (f1)$$

the operator $<x_i(t)>$ denoting a temporal mean of the signal $x_i$, for example over the duration of the experiment.

When the noise is correlated, a possible fusion strategy can be based on the differential measurement described above, according to the following formula:

$$X(t) = \frac{1}{N}\sum_{i=1}^{N} \frac{xi(t) - <xi(t)>}{<xi(t)>} - \frac{xref(t) - <xref(t)>}{<xref(t)>} \quad (f2)$$

where $x_{ref}(t)$ is the output signal of a reference resonator (or of a network of resonators, optionally composed of different groups of resonators), which is not arranged in the same fluid channel or which is arranged in the same channel but which exhibits a response to the gas sample independent from that of the network used for the measurement.

Naturally, those skilled in the art will be able to implement any other algorithm without departing from the scope of the present invention.

Experimental Validation of the System

The inventors have validated the performances of the system described above experimentally.

In a first approach, to validate the reading technique, the tested networks were composed of a plurality of resonators each exhibiting a different natural resonant frequency (in other words, each group of resonators was composed of a single resonator).

To show the possibility of removing fluctuations external to the network, a first experiment consisted in producing a network of 4 resonators exhibiting different resonance frequencies.

Said resonators were connected in parallel and linked to the same reading device, which was designed to read the signals of each resonator by way of the frequency addressing technique described above. The electrical architecture was that represented in FIG. 6.

FIG. 7 shows the signal (df/f) as a function of time for each of the four resonators NEMS1 to NEMS4, the measurement being carried out in air, at atmospheric pressure.

In this case a strong correlation of the signals output by the different resonators is observed.

In this case, the prevalent noise source is the pink noise of the reading device.

It is however possible to remove this noise by applying the fusion algorithm defined by the formula (f2) to the mean of the signals of the resonators NEMS1 to NEMS4, the reference resonator being the resonator NEMS1 here.

It was observed that the signal reconstructed using this fusion exhibits a strong attenuation of the pink noise.

FIG. 8 thus exhibits the power spectral density (DSP expressed in dB/Hz) for the signals output by each of the resonators NEMS1 to NEMS4 and for the reconstructed signal X.

A gain is observed in the order of 20 dB in the power spectral density over the band between 0 and 0.1 Hz.

Figure 9:
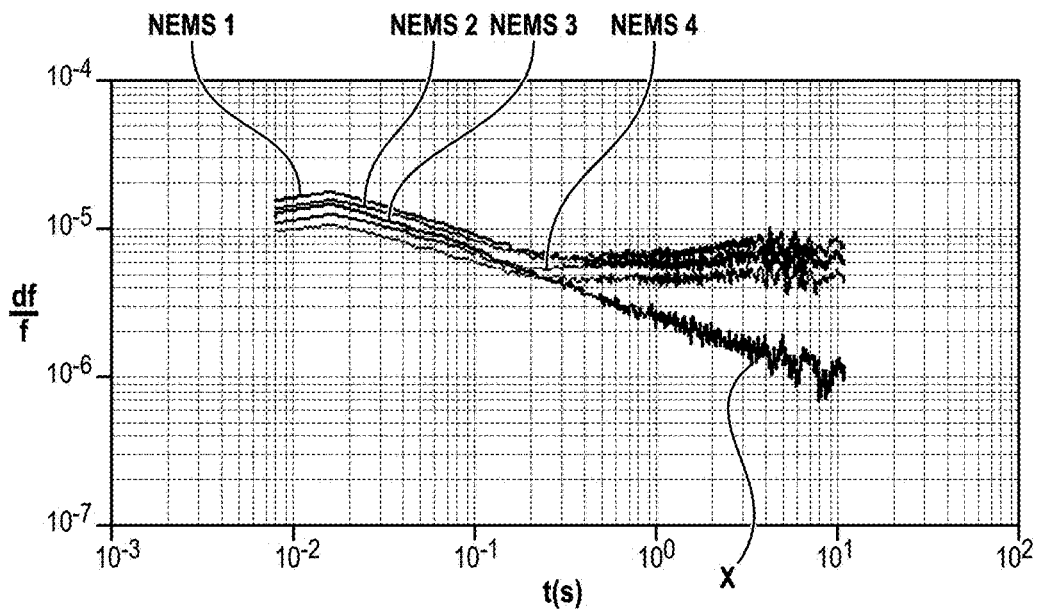
FIG. 9 shows the Allan variance of the signals of each of the resonators and of the signal reconstructed by fusion of said signals.

This improvement can also be observed in the Allan variance which is illustrated in FIG. 9. Indeed, a bijection exists between the power spectral density and the Allan variance.

Thus, a reduction is observed in the Allan variance along a constant slope in a band of the integration period corresponding to pink noise, for which the Allan variance of each of the resonators is static.

Thus, in the case where the prevalent noise source is external to the resonators (which is typically the case of the reading electronics), the networking of the resonators eliminates this noise by employing a fusion technique as described above.

A second experiment was conducted to show the capacity of the system for reducing noise sources intrinsic to the resonators.

In this experiment, a network of 45 resonators was produced and measured in air, at atmospheric pressure.

The signal equivalent to the 45 signals was reconstructed by the fusion algorithm according to the formula (f1).

Figure 10:
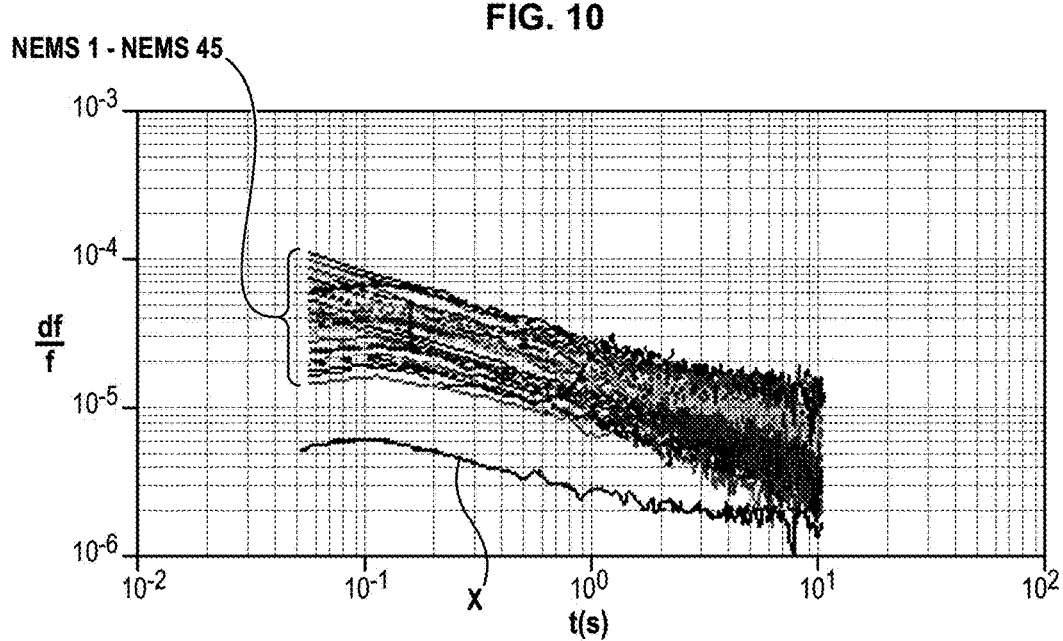
FIG. 10 shows the Allan variance measured for a network of 45 resonators, and for a signal reconstructed from said signals.

FIG. 10 shows the Allan variance for each of the 45 resonators NEMS1 to NEMS45 and for the reconstructed signal X.

An improvement was observed in the Allan variance by a factor of around $\sqrt{45}=6.7$ in the white noise, which shows that the network effect was obtained.

A similar experiment was carried out in a vacuum with a network of 16 resonators.

The signal equivalent to the 16 resonators was reconstructed by the fusion algorithm according to the formula (f1).

Figure 11:
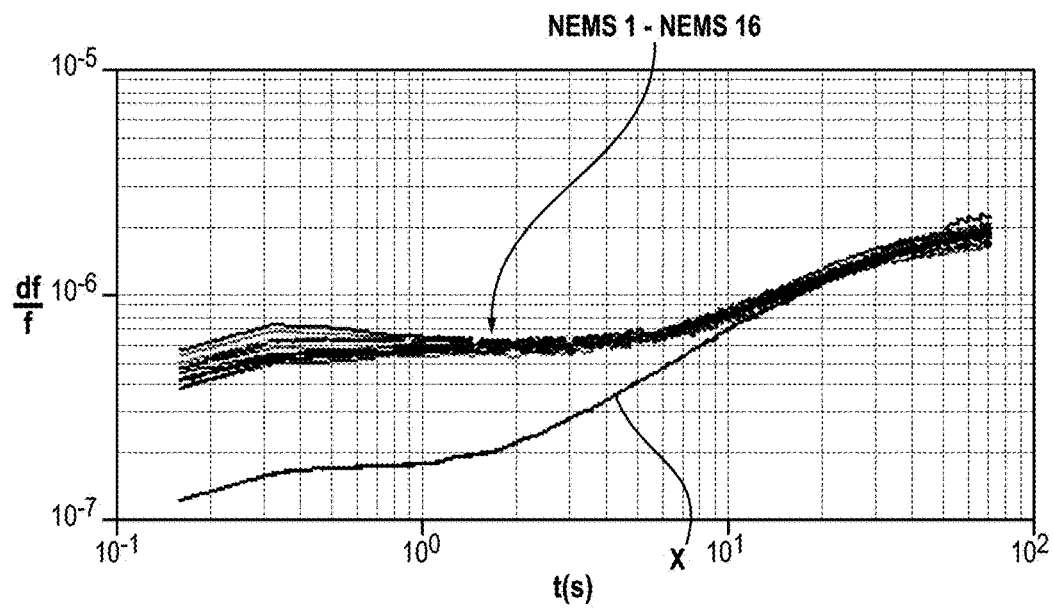
FIG. 11 shows the Allan variance measured for a network of 16 resonators, and for a signal reconstructed from said signals.

FIG. 11 shows the Allan variance for each of the 16 resonators NEMS1 to NEMS16 and for the reconstructed signal X.

An improvement was observed in the Allan variance by a factor of around $\sqrt{16}=4$ in the white noise, which shows that the network effect was obtained.

In this case, the pink noise source is intrinsic to the resonators.

In the long term, a drift in the Allan variance is observed which is due to a correlation in the noise of the resonators. It is however possible to avoid this drift by taking differential measurements as described above.

Another experiment was carried out with a network composed of a group of 75 resonators all exhibiting the same natural resonant frequency.

Figure 12:
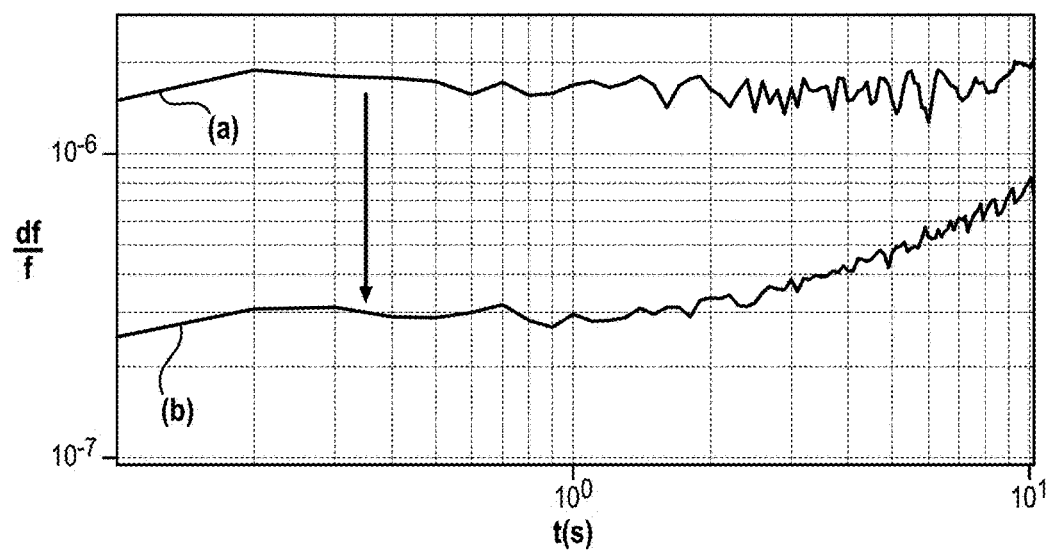
FIG. 12 shows the Allan variance measured for a network of 75 resonators and for a single resonator.

FIG. 12 illustrates the Allan variance for a single resonator (curve (a)) and for said group of resonators (curve (b)), within the range of integration times corresponding to pink noise.

A reduction of a factor approximately equal to 6 is observed for the group of resonators, which is relatively close to the expected network effect ($\sqrt{75}=8.66$).

Finally, an experiment was performed showing the improvement of the detection limit in the case of the group of 75 resonators cited above compared with a single resonator, by sequentially injecting three samples of toluene into the group of resonators and the single resonator.

Figure 13A:
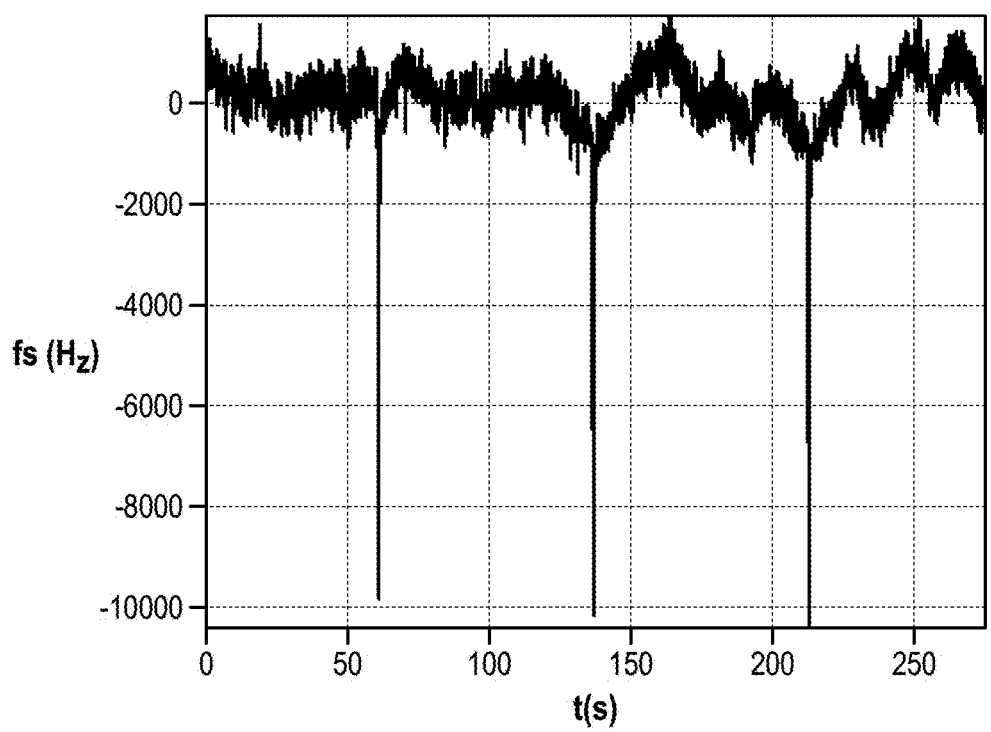
FIGS. 13A and 13B show detection signals of toluene peaks measured by a single resonator and by a group of 75 resonators respectively.
Figure 13B:
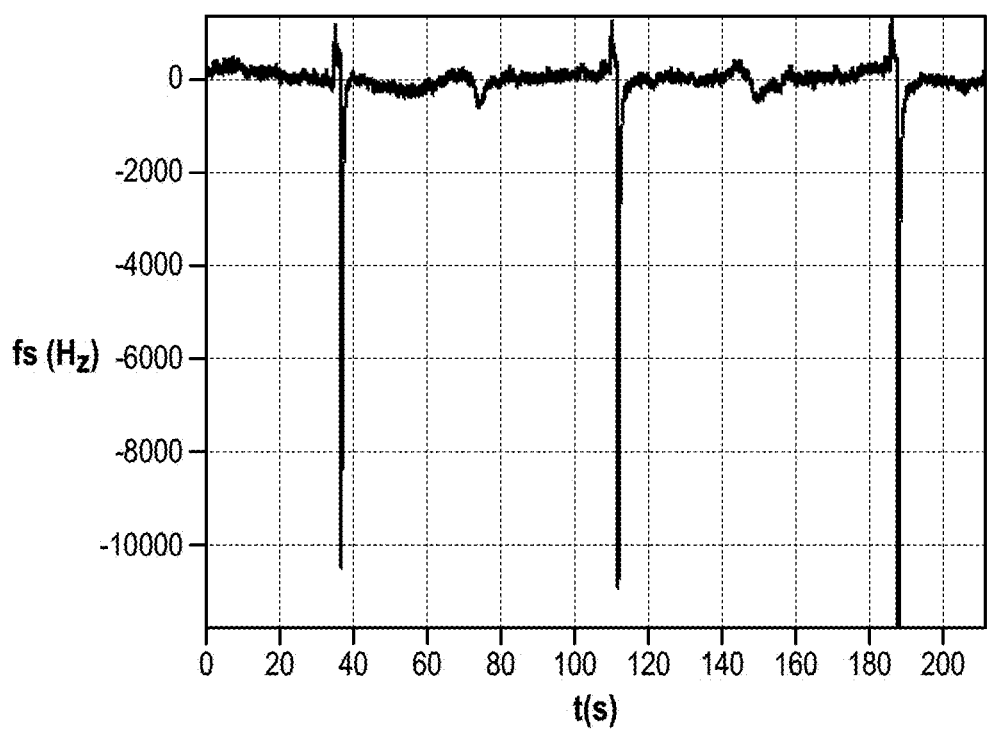

FIG. 13A illustrates the frequency shift fs for the single resonator. It can be observed that the noise is substantially lower than in the first case.

Finally, FIG. 13C shows the superimposition of the curves from FIGS. 13A (curve (a) and 13B (curve (b)), which shows that the noise is substantially reduced with the group of resonators, in such a way that the detection limit is significantly improved.

Method of Fabrication of the Network

Due to the implementation of piezoresistive detection by means of strain gauges made of doped semiconductor material, it is possible to produce each resonator on a substrate of said semiconductor material by way of microelectronics techniques, including photolithography and etching.

Advantageously, said semiconductor material is silicon.

To connect the resonators in a network, two interconnection levels are produced by metallization, and interconnect vias are formed to connect these levels.

Particularly advantageously, the resonators of the network are fabricated collectively on a part of a substrate, which can then be individualized to form a chip bearing said network.

It is thus possible to produce, from a silicon substrate of 200 or 300 m in diameter, a plurality of chips each bearing one or more networks.

Such a chip has micrometer-scale dimensions which allow it to be arranged in a fluid stream of a gas analysis system.

Moreover, the different groups of resonators can be functionalized by a single chemical species, the uniformity of which is ensured by physical or chemical vapor phase deposition techniques (PVD or CVD).

Alternatively, the different groups of resonators forming the network can be functionalized with different chemical species, according to the species contained in the gas sample to be analyzed.

A PVD or CVD deposition is then carried out selectively on the group(s) to be functionalized, for example by way of a technique known as "lift-off" or by stencil masking.

As mentioned above, one advantage of this resonator design is that reduces process variation.

It is thus estimated that variations are attained of below 0.1% in the resonant frequency of the resonators belonging to one and the same group within the network.

These variations can therefore be considered as negligible to the operation of the network.

REFERENCES

[Bargatin2012] I. Bargatin, E. B. Myers, J. S. Aldridge, C. Marcoux, P. Brianceau, L. Duraffourg, E. Colinet, S. Hentz, P. Andreucci, M. L. Roukes, Large-Scale Integration of Nanoelectromechanical Systems for Gas Sensing Applications, NanoLetters 12, 1269-1274 (2012)

[Mile2010] E. Mile, G. Jourdan, I. Bargatin, S. Labarthe, C. Marcoux, P. Andreucci, S. Hentz, C. Kharrat, E. Colinet, L. Duraffourg, In-plane nanoelectromechanical resonators based on silicon nanowire piézorésistiyes detection, Nanotechnology 21, (2010) 165504

WO 2011/154363
EP 2 008 965
WO 2012/034990
WO 2012/034951
WO 2011/154362

The invention claimed is:

1. A measurement system comprising a network of nano-electromechanical system (NEMS) resonators, wherein:
each of said resonators comprises:
an input for receiving an excitation signal and an output for supplying an output signal in response to said excitation signal, said output signal exhibiting resonance at a resonant frequency of the resonator,
a beam suspended with respect to a support, the natural resonant frequency of the resonator corresponding to a natural resonant frequency of said beam,
an electrostatic activation device capable of generating a vibration of said beam under the effect of said excitation signal,
at least one piezoresistive strain gauge made of doped semiconductor material, suspended with respect to said support and extending from the beam in such a way as to detect a displacement of said beam, the variation in electrical resistance of said at least one gauge supplying said output signal,
said network comprises at least two groups of resonators, each group comprising at least two resonators exhibiting an identical natural resonant frequency, each group of resonators exhibiting a different natural resonant frequency from that of each other group,
the system comprises a memory wherein an item of information relating to the natural resonant frequency of each resonator or group of resonators is stored,
the resonators forming each group are connected in parallel, each group comprising an input and an output respectively connected to the input and output of each of said resonators,
the groups of resonators forming said network are connected in parallel, said network comprising an input and an output respectively connected to the input and the output of each of said groups of resonators, and
said system comprises a reading device designed to supply an excitation signal to the input of the network and to determine the resonant frequency of a selected group of resonators by injecting into said excitation signal a frequency component corresponding to the natural resonant frequency stored in the memory for each selected group of resonators and by identifying, in the output signal of the network, a frequency component at the resonant frequency of the selected group of resonators.

2. The system according to claim 1, further comprising a device for summing the output signals of each group of resonators of the network into a total output signal of the network, and wherein the reading device is designed to determine the resonant frequency of a group of resonators from said total output signal of the network.

3. The system according to claim 2, wherein said reading device comprises a phase-locked loop (PLL) designed to lock a frequency of the excitation signal onto the frequency of a resonance peak of the output signal of the network and to supply the locked frequency as the excitation resonant frequency.

4. The system according to claim 1, wherein each group of resonators is functionalized with a different chemical species.

5. The system according to claim 1, wherein the resonators of the network are arranged on one and the same support in such a way as to form rows and columns of resonators running parallel to one another, the beams of the resonators being parallel to one another.

6. The system according to claim 1, wherein the resonators of the network are arranged on a common support in rows and columns, wherein each row of resonators includes at least two adjacent resonators that are symmetrical with one another over a plane of symmetry that is parallel to the columns of resonators.

7. The system according to claim 1, further comprising at least one fluid channel intended for a flow of a gas sample to be analyzed, said network of resonators being arranged in said fluid channel in such a way that the beams of said resonators are exposed to said sample.

8. The system according to claim 7, further comprising at least two networks of resonators in said fluid channel.

9. The system according to claim 7, further comprising at least one said reference resonator arranged outside the fluid channel and connected to the same reading device as the network arranged in the fluid channel, and a processing system configured to combine the output signal of said reference resonator with the output signals of the groups of resonators of the network.

10. The system according to claim 7, wherein the network comprises at least one said reference resonator configured to be less sensitive to the gas sample than the other groups of resonators, and the system comprises a processing system configured to combine the output signal of said reference resonator with the output signals of the groups of resonators of the network.

11. The system according to claim 7, further comprising a gas chromatography column containing said fluid channel.

12. The system according to claim 11, wherein the channel of said chromatography column comprises a plurality of resonator networks distributed regularly between the input and the output of said column.

13. The system according to claim 7, further comprising a gas chromatography column upstream of said fluid channel in the direction of flow of the gas sample.

14. A method for reading a system according to claim 1, comprising the steps consisting in:
  selecting a group of resonators to be read, from among the groups of resonators of the network,
  retrieving from the memory the natural resonance information of each selected group of resonators,
  applying an excitation signal to the network comprising a frequency component corresponding to the natural resonant frequency of each selected group of resonators,
  determining the resonant frequency of each selected group of resonators by identifying, in the output signal of the network, a resonant frequency component of each selected group of resonators.

15. The method according to claim 14, wherein the application of said excitation signal generates in the output signal a core frequency component corresponding to the resonance of each selected group of resonators, and the resonant frequency of each selected group of resonators is determined by extracting said frequency component from the output signal of the network.

16. A process of fabrication of a system according to claim 1, comprising the collective fabrication, on a support made of a semiconductor material, of the resonators forming said network by employing microelectronics techniques.

17. The process according to claim 16, further comprising the collective functionalization of the groups of resonators of said network by chemical vapour deposition (CVD) or physical vapour deposition (PVD) of different chemical species for each of said groups.

* * * * *